US006530096B1

(12) United States Patent
Mayhew et al.

(10) Patent No.: US 6,530,096 B1
(45) Date of Patent: Mar. 11, 2003

(54) FOOT REJUVENATION SHOWER APPARATUS

(76) Inventors: Kimberly K. Mayhew, 643 Arvana, Houston, TX (US) 77034; Amanda J. Watkins, 643 Arvana, Houston, TX (US) 77034

( * ) Notice: Subject to any disclaimer, the term of this patent is extended or adjusted under 35 U.S.C. 154(b) by 0 days.

(21) Appl. No.: 09/695,362

(22) Filed: Oct. 24, 2000

(51) Int. Cl.[7] ................................................ A47K 3/02
(52) U.S. Cl. ................................................ 4/583; 4/580
(58) Field of Search .......................... 4/580, 581, 582, 4/583; 132/76.4, 75.6; 428/172

(56) References Cited

U.S. PATENT DOCUMENTS

| | | | | |
|---|---|---|---|---|
| 1,534,214 A | * | 4/1925 | Holt ................................ 4/583 |
| 2,503,174 A | * | 4/1950 | Salvadore ........................ 4/661 |
| 4,246,914 A | * | 1/1981 | Keyser ........................ 132/76.4 |
| 4,625,344 A | | 12/1986 | Howard .......................... 4/581 |
| 4,712,552 A | * | 12/1987 | Pangburn ...................... 128/355 |
| 4,849,271 A | * | 7/1989 | Weihrauch ...................... 428/88 |
| 4,931,330 A | | 6/1990 | Sttier et al. ...................... 428/40 |
| 4,956,882 A | | 9/1990 | Cohn, III ........................ 4/580 |
| 5,069,951 A | | 12/1991 | Egan ............................ 428/172 |
| D343,476 S | * | 1/1994 | Tomsick ........................ D28/63 |
| 5,482,759 A | * | 1/1996 | Primeau ........................ 428/167 |
| 5,575,034 A | * | 11/1996 | Biernacinski et al. .......... 15/217 |
| 5,781,941 A | | 7/1998 | Radke et al. .................... 4/583 |
| 5,913,313 A | * | 6/1999 | Brunderman ................ 132/76.4 |
| 5,919,540 A | * | 7/1999 | Bailey ............................ 428/67 |
| 5,962,350 A | * | 10/1999 | Krotine ........................ 442/370 |
| 5,996,160 A | * | 12/1999 | Pruitt ........................ 15/104.92 |
| 6,202,689 B1 | * | 3/2001 | Williams ...................... 137/602 |

* cited by examiner

Primary Examiner—Gregory Huson
Assistant Examiner—Huyen Le
(74) Attorney, Agent, or Firm—The Matthews Firm

(57) ABSTRACT

An improved apparatus and related method of use is disclosed that may be used in a shower to remove dead skin from a foot of a user. The apparatus generally is constructed of a lower surface that is releasably engaged with a floor and an upper portion with a selectively applicatable upper surface for removing dead skin of a foot of a user.

7 Claims, 3 Drawing Sheets

FOOT REJUVENATION SHOWER APPARATUS

TECHNICAL FIELD

The present invention relates generally to an apparatus for foot beautification and rejuvenation and related methods of use.

BACKGROUND ART

The health of humans feet has become an ever more priority in recent years with people spending an increased time in shoes while walking on concrete or other hard surfaces. As partial solutions to this problem, technology has developed whereby the soles of shoes or the foot portion of a sock are padded. However, even with all these advancements in foot care, feet still dry out. This often results in large callous123d or rough portions developing on soles of feet and in the heel region of the foot.

These rough portions of the foot have been known to cause discomfort both to the person the foot belongs to and others. A common solution to this problem has been the use of an abrasive pad or stone to scrape the dead skin off the feet. A common form of abrasive is a pumice stone. However, this requires excessive amounts of time. Therefore, many people forgo the use of an abrasive and do not remove the rough portions of the feet. Accordingly, the art field desires a quick and effective apparatus and method for removing roughened portions of the feet that does not require excessive time.

A location where many people spend time daily is the shower or bath. People commonly take showers to clean themselves. It is common in showers to place a mat on the shower or bath floor to prevent slippage and accidental falls. The majority of these shower mats use a texturized upper surface to increase a coefficient of friction between the foot of a user and the shower mat, thereby preventing slips and falls within the shower.

A common example in the art field is found in U.S. Pat. No. 4,931,330 to Stier et al. This patent discloses a prefabricated, slip resistant surface coating comprising sheet members having a plurality of embedded, finely divided particles. While this apparatus may aid in preventing slips and falls within a shower, it does not provide an abrasive surface capable of removing dead skin from a foot of a user. Further, this apparatus does not have an upper surface that may be removed and replaced with another surface. Accordingly, the art field is in need of a slip resistant bath mat that allows a user to remove dead skin from their feet while allowing the removing and replacing of the upper surface.

Another prior art shower or bath mat is disclosed in United States Pat. No. 5,069,951 to Egan. This patent discloses a magnetized bath mat that is removably connected to a magnetically attractive bottom of a bathtub or shower. The bath mat of this invention incorporates a magnetic layer disposed beneath a slip resistant top surface. However, the slip resistant upper surface is not capable of removing dead skin from a foot of a user. Further, this apparatus does not have an upper surface that may be removed and replaced with another surface. Accordingly, the art field is in need of a slip resistant bath mat that allows a user to remove dead skin from their feet while allowing the removing and replacing of the upper surface.

SUMMARY OF THE INVENTION

The present invention generally relates to an apparatus and related method of use for removing dead skin from a foot of a user. Various embodiments of the present invention incorporate a roughened upper surface and a lower surface that may be releasably attached to a floor, such as a bathtub or a shower floor.

This summary is not intended to be a limitation with respect to the features of the invention as claimed, and this and other objects can be more readily observed and understood in the detailed description of the preferred embodiment and the claims.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

GENERAL DESCRIPTION AND PREFERRED MODE FOR CARRYING OUT THE INVENTION

Figure 1A:
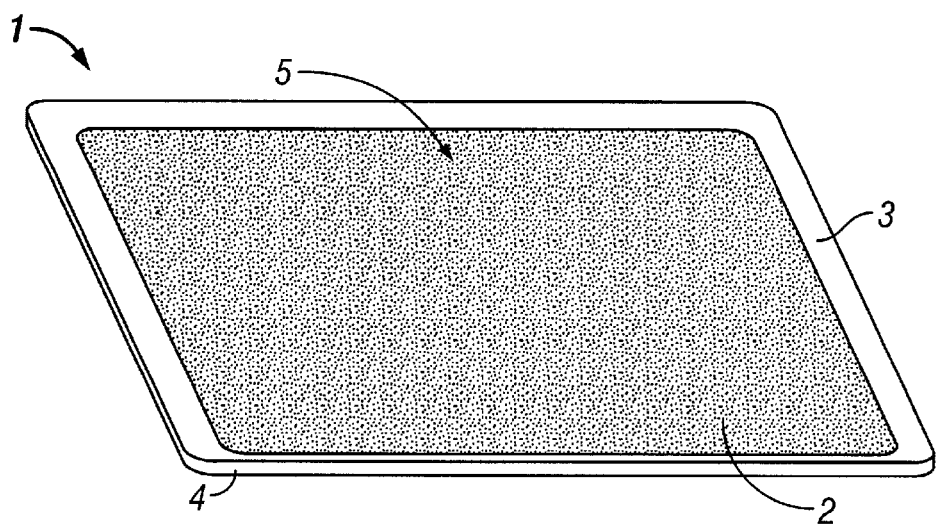
FIG. 1a is an illustration of an embodiment of the present invention.
Figure 1B:
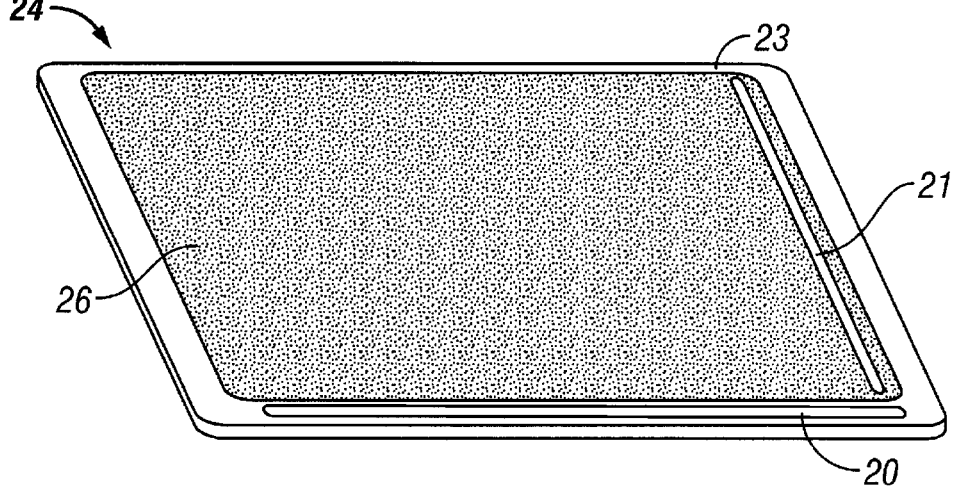
FIG. 1b is an illustration of an alternate embodiment of the present invention.
Figure 2:
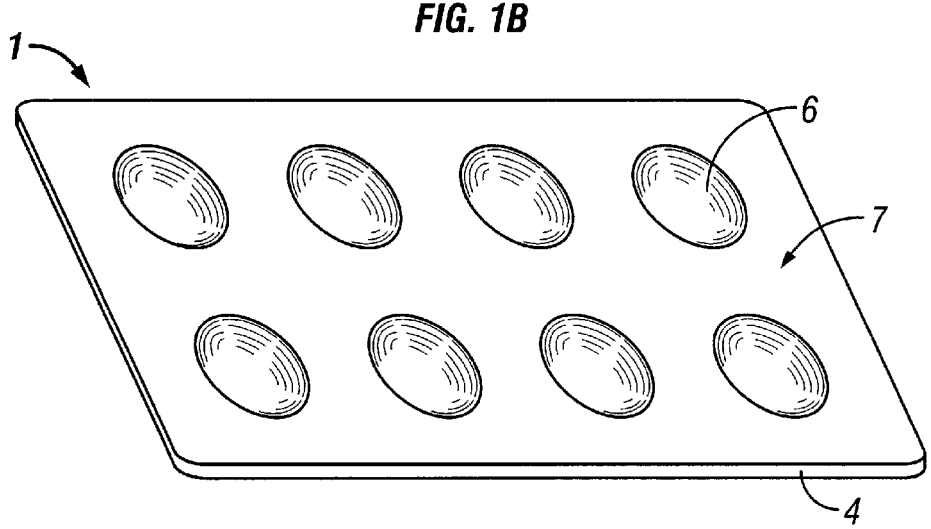
FIG. 2 is an illustration of an underside of the embodiment from FIG. 1.

Referring now to FIGS. 1 and 2, an illustration of an embodiment of the present invention, general features of the embodiment may be observed. Mat 1 has an upper surface 5 and a lower surface 7. Mat 1 may be constructed of any material common in the art such as a plastic, a vinyl, a composite, or a rubber. Mat 1 has a side surface 4 extending between upper surface 5 and the lower surface 7. Side Surface 4 may be of any thickness and may be constructed of any number of layers to provide for strength and durability. In a most preferred embodiment, mat 1 is pliable about side surface 4 to allow for ease of installation and movement.

In a most preferred embodiment, at least a portion of the upper surface 5 has an abrasive portion 2. This abrasive portion may be formed from any material common in the art. In a preferred embodiment, the abrasive portion is pumice, for example, from a pumice stone. However, various other embodiments use natural and synthetic substances such as plastic, gravel, rock, and/or sand.

The abrasive portion 2 may be mounted or connected to mat 1 be any means common in the art such as an adhesive. Various embodiments of the present invention incorporate abrasive portion 2 as the upper surface 5 of mat 1 or blend the abrasive portion 2 with the upper surface 5 such that the upper surface 5 in and of itself retains an abrasive characteristic capable of removing dead skin from a foot of a user as the user is passing a roughened portion of their foot over the abrasive portion.

The dimensions of mat 1 may vary according to a the dimensions of the respective bath or shower floor to be covered. Preferred embodiments utilize a mat 1 that is large enough to provide user movement about a portion of the floor of the bath or shower without contact with lip 3. However, sheets of the afore-mentioned size are strictly for comfort issues and mat 1 may be of any size; not limited to a particular size, shape or dimension.

An alternate preferred embodiment of the present invention utilizes mat 1 having a lip 3 that extends about at least a portion of the perimeter of upper surface 5. Lip 3 may be connected to mat 1 by any means common in the art such as an adhesive or snap-lock system. A snap lock system is advantageous because the snap-lock system allows lip 3 to be removed for cleaning. Other embodiments of the present invention have a lip 3 that is an integral portion of mat 1.

In a preferred embodiment, lip 3 extends over a portion of upper surface 5 whereby a portion of lip 3 is in close proximity to upper surface 5. A sheet or layer (shown in FIG. 3 and FIG. 4) of abrasive portion 2 or other surface may be slid or placed under lip 3 such that lip 3 secures or holds abrasive portion 2 on upper surface 5. The sheet is releasably secured by lip 3 such that a user may selectively remove and insert the same sheet or a different sheet within a portion of lip 3. This feature allows a user to select various surfaces for placement on upper surface 5 or to clean the sheet 2. Upper surface 5 may incorporate ridges or gnarls for further securing of the sheet or layer. Ridges or gnarls will aid in preventing accidental slips or falls within the bathtub or shower.

Various embodiments of the present invention incorporate a lip 3 that extends around edges of mat 1. A preferred embodiment utilizes a lip 3 that extends about three quarters of mat 1 along the edge. A most preferred embodiment utilizes a lip 3 that extends about the entire perimeter of mat 1. However, various other embodiments incorporate a lip 3 that extends over various other portions such that lip 3 is able to assist retaining sheet 2 on mat 1 during use. Now referring to FIG. 1b, an illustration of an alternate embodiment of the present invention, a most preferred embodiment of the present invention utilizes a mat 24 and an edge 23 that extends completely around mat 24 with a trough 20 extending about at least a portion of mat 24 along edge 23. Preferably, trough 20 extends about the entire portion of edge 23 with a slit 21 along at least one (1) portion of lip for retaining abrasive portion 26. Abrasive portion 26 may be fitted along upper portion 25 such that an edge of abrasive portion 26 is along trough 20 with another portion of abrasive portion 26 fed through a portion of slit 21. Slit 21 may extend through mat 24 such that slit 21 provides a communication port with lower surface 7 (not shown). Abrasive portion 26 may be integral with mat 24 or may be a separate sheet as described above.

Referring further to FIG. 2, an illustration of an underside of the embodiment from FIG. 1, a manner of securing mat 1 to a floor is disclosed. Various embodiments of the present invention use devices common in the art for securing a connection of mat 1 to the floor of a shower or bath. A preferred embodiment utilizes one or more conventional suction cups 6 mounted to lower surface 7. The suction cup 6 is adapted for releasable connection with a floor, such as a bath or shower floor. However, other embodiments of the present invention utilize magnetic portions, adhesive portions or roughened portions to maintain a firm contact with the floor. Other embodiments of suction cups 6 utilize a tab (not shown) for assisting in disengaging suction cup 6 with the floor. Further, various other embodiments utilize a magnetic base that is first removably adhered to a tile floor of a shower and then an embodiment of the present invention with a magnetic portion may be utilized and secured to the floor via the magnetic portion adhered to the floor.

Figure 3:
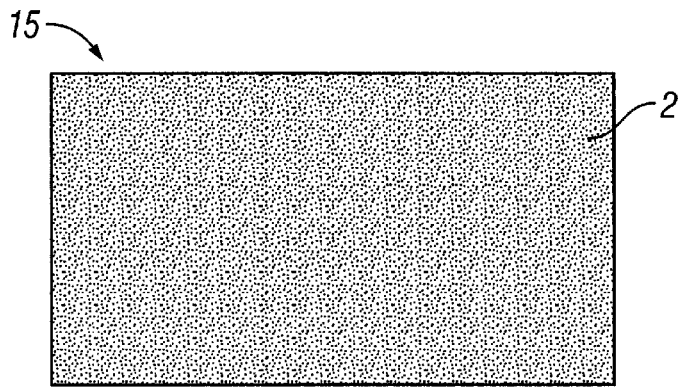
FIG. 3 is an illustration of an embodiment of a sheet of an abrasive material that may used in various embodiments of the present invention.

Now referring to FIG. 3, an illustration of an embodiment of a sheet of an abrasive material that may used in various embodiments of the present invention, a sheet 15 is disclosed. Generally, sheet 15 is cut in such a manner that sheet 15 fits within a portion of the lip 3 on an upper surface of a mat as illustrated in FIG. 1. Preferred embodiments of sheet 15 utilize an abrasive portion 2 mounted to or integral with sheet 15. A most preferred embodiment utilizes a pumice material that is mounted or adhered on a paper like material, such as cardboard or portions of paper, to facilitate changing and maneuverability of sheet 15. However, other embodiments utilize a pliable material such as rubber or plastic that is affixed with or integral with abrasive portion 2.

Figure 4:
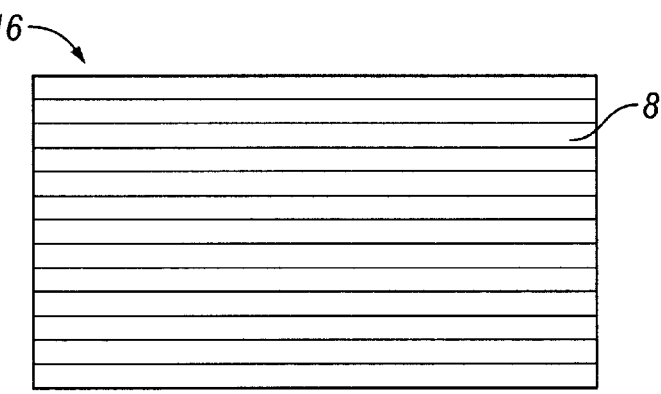
FIG. 4 is an illustration of an embodiment of a sheet of a slip resistant material that may used in various embodiments of the present invention.

Now referring to FIG. 4, an illustration of an embodiment of a sheet of a slip resistant material that may used in various embodiments of the present invention, an alternate sheet of material is disclosed. The present invention envisions adaptability of design to allow for an interchangeable use of an abrasive sheet (not shown) and a slip resistant sheet 16. In this manner, a user may change to a sheet of an abrasive material for removing the dead skin from their feet as needed and switch back to a slip resistant sheet 16 for normal usage. A discontinuity 8 is on a surface of slip resistant sheet 16 to aid in the prevention of accidental falls in an environment that is slippery, such as a shower or bath floor. The discontinuity 8 may be of any kind common in the art such as ridges, gnarls, bumps and the like.

Figure 5:
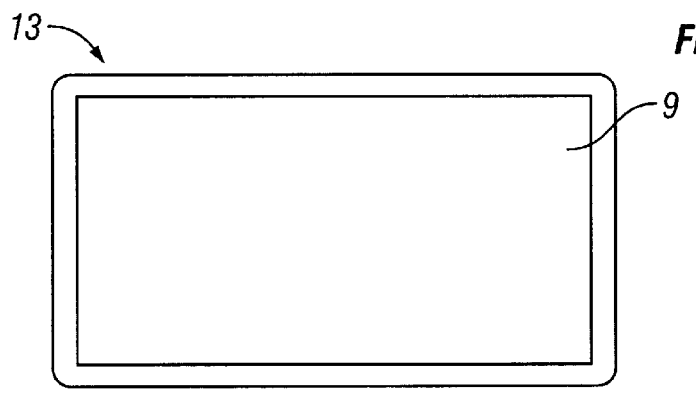
FIG. 5 is an illustration of an alternate embodiment of the present invention utilizing a magnetic portion for releasable connection of a lower surface to a floor.

Now referring to FIG. 5, an illustration of an alternate embodiment of the present invention utilizing a magnetic portion for releasable connection of a lower surface to a floor, a magnetic portion 9 is disclosed for securing a connection of lower surface 13 to a floor. Magnetic portion 9 is most advantageous in an environment in which the floor is a metal and capable of magnetic attraction. The arrangement of magnetic portion 9 on lower surface 13 may be a solid sheet covering the entirety of lower surface 13 or portions of a magnetic portion arranged about lower surface 13.

Figure 6:
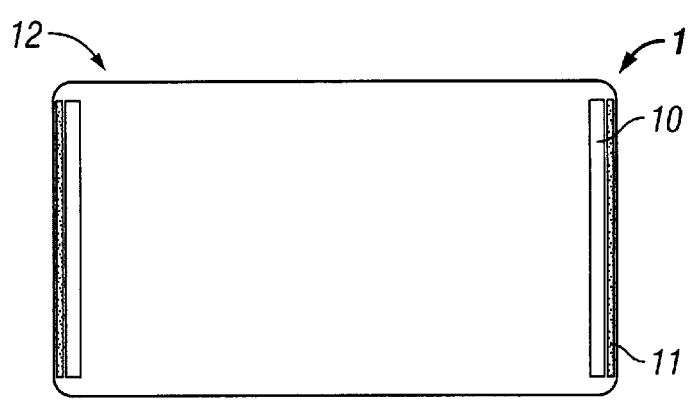
FIG. 6 is an illustration of an alternate embodiment of the present invention utilizing a clip for securing a liner.

Now referring to FIG. 6, an illustration of an alternate embodiment of the present invention utilizing a clip for securing a liner, a clip is disclosed for securing a sheet on upper surface 12. A clip 10 may positioned about mat 1 in any manner. Various embodiments utilize multiple clips positioned about the edges of upper surface 12 to releasable secure a sheet or other surface on upper surface 5. A preferred embodiment utilizes a clip 10 with a spring 11 to bias a partially rigid portion of clip 10 into a position whereby clip 10 secures a sheet (not shown). A most preferred material for construction of clip 10 and spring 11 is a plastic to prevent rust and other disintegration of clip 10 and spring 11. However, various other embodiments of the present invention utilize clips of 7 differing configuration that enable a user to releasably secure a sheet or layer to upper surface 12.

Figure 7:
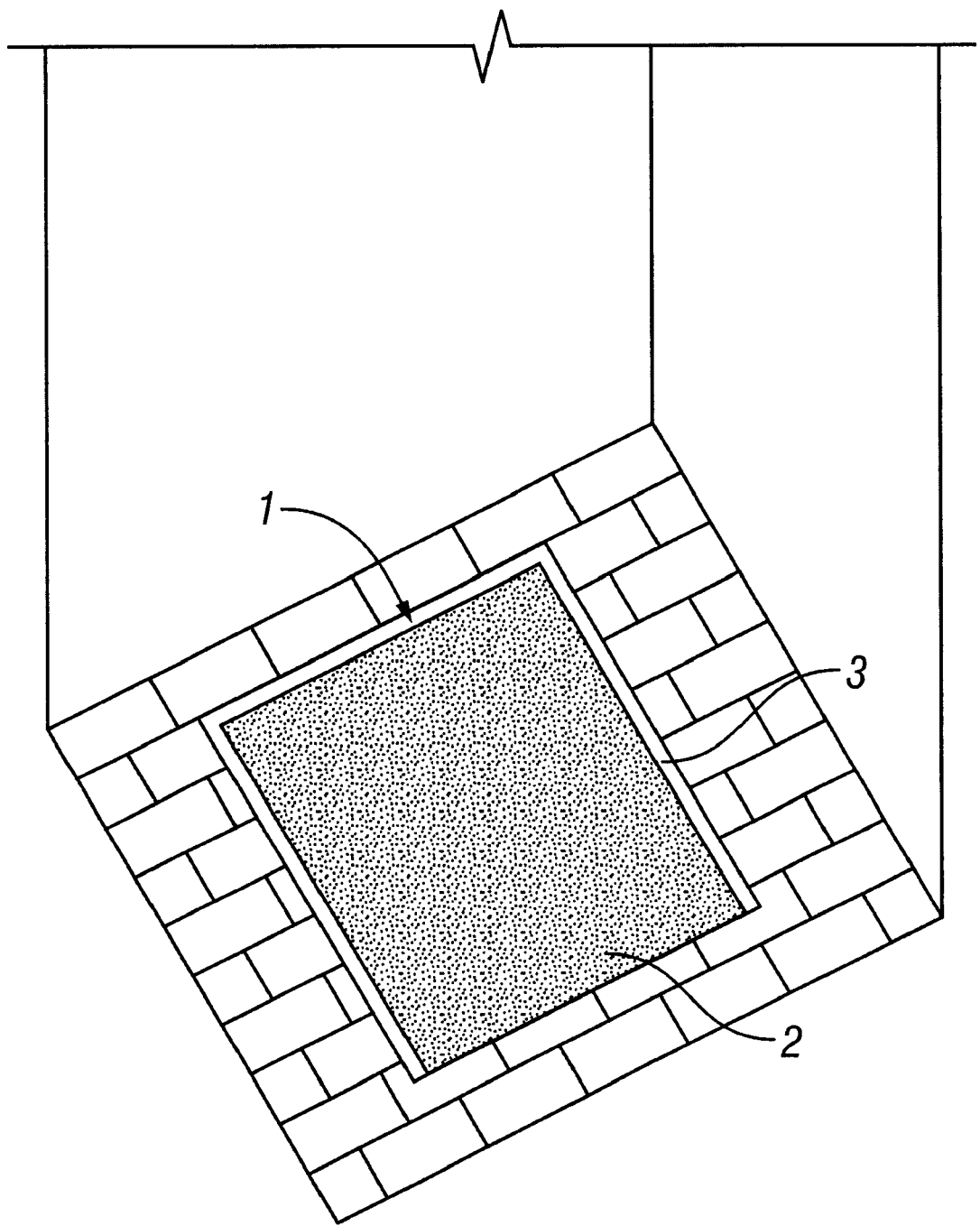
FIG. 7 is an illustration of an embodiment of the present invention installed on an embodiment of a shower floor.

Now referring to FIG. 7, an illustration of an embodiment of the present invention installed on an embodiment of a shower floor, the utility of the present invention may become more readily apparent. Mat 1 may be placed on a floor of a shower or bathtub such that a lower surface is releasably secured or fixedly secured about the floor. A user may then step onto the mat without the fear of slipping on the moist or wet floor. In a most preferred embodiment, a user begins by stepping onto the mat and then passing their foot over an abrasive portion of the mat to remove the dead and roughened portions of skin about the feet. The user may perform such tasks while cleaning themselves in the shower or bathtub, thereby not requiring excess time for foot rejuvenation and beautification. When the user has removed an appropriate amount of skin or is finished with foot beautification and rejuvenation, the user may remove abrasive portion 2 from lip 3 and place a slip resistant surface under a portion of lip 3. As well, the cleaning of the floor and the mat 1 is made relatively easy by the ability of embodiments of the present invention to be dissassembled for cleaning and replacement.

While a single method and a few embodiments of devices have been shown and described, it will be understood that the invention is not limited thereto, since many modifications may be made and will become apparent to those of ordinary skill in the art.

What is claimed is:

1. A new and improved method for foot rejuvenation comprising the steps of stepping a foot onto a first abrasive surface on a mat that is releasably secured to a floor, wherein the first abrasive surface is releasably connected to the mat; passing the foot across the first abrasive surface; and, removing dead skin from the foot.

2. The method of claim 1, further comprising the steps of removing the first abrasive surface and replacing the abrasive surface with a second surface.

3. The method of claim 1, further comprising the step of running water in the bath or shower whereby the foot is moistened as the foot is passing across the first abrasive surface.

4. The method according to claim 1, wherein the mat is releasably secured to the floor by at least one magnet.

5. The method according to claim 1, wherein the mat is releasably secured to the floor by at least one suction cup.

6. The method according to claim 1, wherein the mat is releasably secured to the floor by an adhesive material.

7. The method according to claim 1, wherein the mat is releasably secured to the floor by at least one roughened surface.

* * * * *